United States Patent [19]
Savard et al.

[11] Patent Number: 6,072,890
[45] Date of Patent: Jun. 6, 2000

[54] AUTOMATIC LUMBER SORTING

[75] Inventors: Marc Savard; François Léger, both of Sainte-Foy, Canada

[73] Assignee: Forintek Canada Corp., Canada

[21] Appl. No.: 09/073,751

[22] Filed: May 6, 1998

[51] Int. Cl.[7] .................................................. G06K 9/00
[52] U.S. Cl. ........................ 382/110; 382/141; 209/518
[58] Field of Search .................................. 382/100, 110, 382/162, 164, 165, 141; 209/517, 518; 250/559.25; 144/391, 392, 398, 402, 408; 239/DIG. 14

[56] References Cited

U.S. PATENT DOCUMENTS

| | | | |
|---|---|---|---|
| 4,934,228 | 6/1990 | Bolton et al. | 83/23 |
| 4,992,949 | 2/1991 | Arden | 700/225 |
| 5,006,225 | 4/1991 | Beauchemin et al. | 209/3.3 |
| 5,071,771 | 12/1991 | Barbour et al. | 436/153 |
| 5,674,335 | 10/1997 | Aman et al. | 156/64 |
| 5,761,070 | 6/1998 | Conners et al. | 700/223 |

OTHER PUBLICATIONS

"Separation of Eastern Spruce and Balsam Fir by Chemical Methods", Kutscha, Lomerson and Dyer, Wood Science and Technology, 1978.

*Primary Examiner*—Andrew W. Johns
*Assistant Examiner*—Shervin K. Nakhjavan
*Attorney, Agent, or Firm*—Barnes & Thornburg

[57] ABSTRACT

To facilitate separation of lumber pieces that are of different species, an indicator liquid is sprayed on to a fresh cut end of each lumber piece to produce a characteristic reaction, e.g. based upon pH. After a suitable interval the coated ends of the lumber pieces are optically scanned, the scanned image being analyzed spectrographically to identify the species of the lumber piece, e.g. as between spruce and fir. The lumber pieces are separated accordingly so that further processing thereof, e.g. kiln drying can be done under optimal conditions for that species.

20 Claims, 3 Drawing Sheets

AUTOMATIC LUMBER SORTING

BACKGROUND OF THE INVENTION (a) Field of the Invention

This invention relates to a new or improved lumber sorting system and in particular to a method and an apparatus for differentiating in a reliable manner lumber pieces of separate species.

(b) Description of the Prior Art

Some lumber sorting systems based on sorting criteria other than the wood species (i.e. moisture content, density, weight) have recently been put on the market. However sorting by species rather than by the above referred to characteristics is recognized by the industry as being a more desirable practice. In particular, sorting by species is anticipated to provide more benefit in lumber drying practice than sorting by weight or moisture content, especially when spruce and fir mixed species are involved.

As has been noted by Kutscha, Lomerson and Dyer in a paper entitled "Separation of Eastern Spruce and Balsam Fir by Chemical Method" 1978, the occurrence of mixed stands of spruce and fir in some regions has led to the practice of harvesting these wood products without separation under the non-specifical label "spruce-fir". However lumber pieces of these two species have many different characteristics, particularly as concerns drying times, shrinkage potential, strength and gluing properties. The time required to dry fir lumber pieces is approximately 50% longer than that to dry spruce pieces so that if there is no separation, the kiln drying schedule must be based on the drying time for fir. This can result in over-drying of the spruce content of the kiln drying load, and because of the tendency of spruce pieces to twist, the product can suffer degradation.

While spruce and fir trees are quite easily distinguished from one another, once the trees have been reduced to lumber, spruce and fir pieces are quite similar in appearance, except for the presence of resin canals in spruce and their absence in fir. However this difference is insufficient and could not form an adequate basis for separation in any production process.

An important proportion, perhaps as much as 80% or more, of lumber currently being produced is kiln dried. One of the biggest challenges facing the industry is to minimize the energy costs of kiln drying and avoid degradation problems that can occur when drying mixed species. Many producers have adopted the use of manual sorting of wood species on a production line prior to drying, and despite the shortcomings of this method, no better technique has so far been developed.

Manual sorting suffers from several drawbacks. The first arises from the fact that the lumber pieces move along the conveyor typically at speeds up to about 175 pieces per minute, which obviously gives the sorter very little time to make any sorting decisions. Furthermore, visually distinguishing one species of wood from another is sometimes difficult. For example recent studies have indicated that the manual method provides an average success rate of only 85% in sorting spruce and fir.

U.S. Pat. No. 4,992,949 Arden describes a system for color sorting of lumber in the manufacture of products where it is important for lumber elements that are used in combination to have an homogenous appearance as regards wood color and slope of the grain. The system of Arden involves the use of a scanning camera to acquire image data and developing a histogram of frequency distribution of colour intensity for various colours. However it is not believed that this prior art system would be applicable to sorting of lumber pieces in accordance with different species of wood.

It is the aim of the present invention to provide a method and apparatus for reliably sorting lumber pieces of different species.

SUMMARY OF THE INVENTION

The present invention provides a method for differentiating lumber pieces of one species from those of another comprising: (a) coating a cut end of each lumber piece with an indicator liquid which is such as to react with the cut end, lumber pieces of a predetermined species producing a reaction product that is characteristic of such species; (b) scanning the coated ends of said lumber pieces produced in step (a) and identifying pieces of said predetermined species through means for recognizing said characteristic reaction; and (c) separating such identified pieces from the remainder of said pieces.

Preferably the sorting is done on a continuous basis, e.g. by sampling every piece of lumber delivered on a conveyor, utilizing an optical device. In preferred embodiments a spray system is positioned at one location alongside the conveyor which in conjunction with sensing devices is triggered to spray a required chemical indicator onto a fresh end cut of each lumber piece. If needed, a saw is installed immediately upstream of the spray system to produce the fresh cut.

The distance between the spray system and the downstream optical recognition apparatus is calculated taking into account the reaction time of the chemical indicator with the wood, and the speed of the conveyor.

The optical system may comprise a light source, lens, filters and detectors fixed on a support platform which can be adjusted to ensure that the system is in proper alignment. The sensing devices are coupled to deliver information signals to a microprocessor which through an algorithm identifies and classifies individual lumber pieces according to species, based on predetermined sorting criteria. A digital signal is delivered by the system and utilized to drive mechanical means to effect physical sorting of the lumber pieces.

The indicator liquid is preferably one that responds to the pH of the wood to produce a colour that is characteristic of the pH, and the optical system is set to recognize the characteristic colour and use it as a basis for differentiating the lumber species.

For differentiating lumber species of spruce and fir, a solution of bromophenol blue is sprayed on a fresh cut end of a lumber piece, producing a chemical reaction that will colour this end in a range covering yellow, green, and dark blue. By measuring the respective reflectivity of many samples over a wavelength band using a spectrograph, it has been established that each specie has a maximum reflectivity at a different wavelength, which will be referred to as its signature. The reflectivity of the second specie at the signature (wavelength) of the first specie is very much lower, and vice versa.

After a suitable interval the end cuts of the lumber pieces are illuminated by a light source and the reflected light is analyzed by an optical system which includes detectors each attuned to a selective different wavelength.

BRIEF DESCRIPTION OF THE DRAWINGS

The invention will further be described, by way of example only, with reference to the accompanying drawings:

Referring to FIG. 1, a continuously moving horizontal conveyor 1 is adapted to carry a series of lumber pieces 2 thereon, the lumber pieces being engaged in spaced relationship by carriers 3 on the conveyor belt or chain 4. The lumber pieces 2 are loaded on to the belt or chain 4 as indicated at the right hand side of FIG. 1A, and are carried by the belt or chain successively past a spraying device 5 and a scanning device 6 as the conveyor belt or chain progresses from right to left as shown in the figure. The cross-grain ends of the lumber pieces 2 are brought into register by alignment means (not shown) so that these ends 10 are at a uniform spacing from the spraying device and from the scanning device, with the lumber pieces being oriented at right angles to the travel direction of the conveyor belt or chain 4.

Figure 1A:
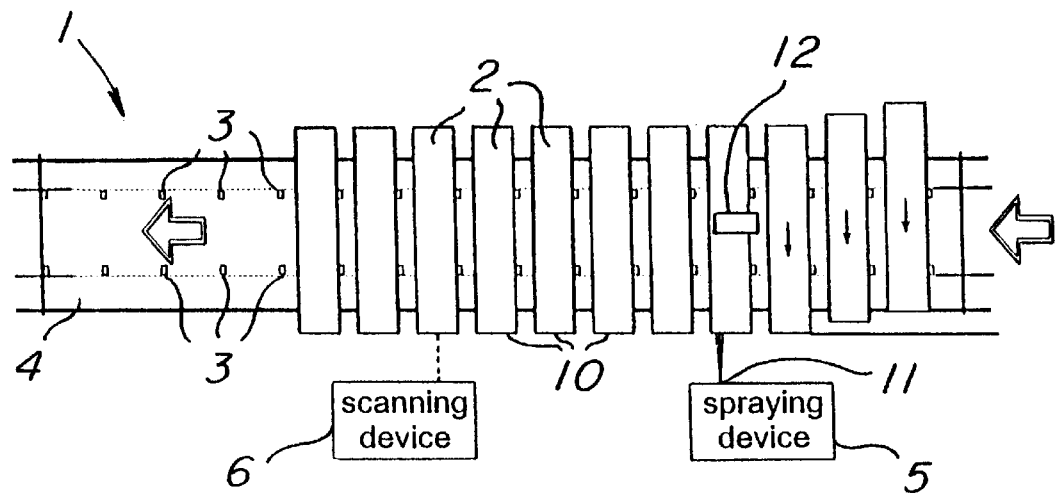
FIG. 1A is a somewhat schematic plan view of a lumber sorting system in accordance with the invention.
Figure 1B:
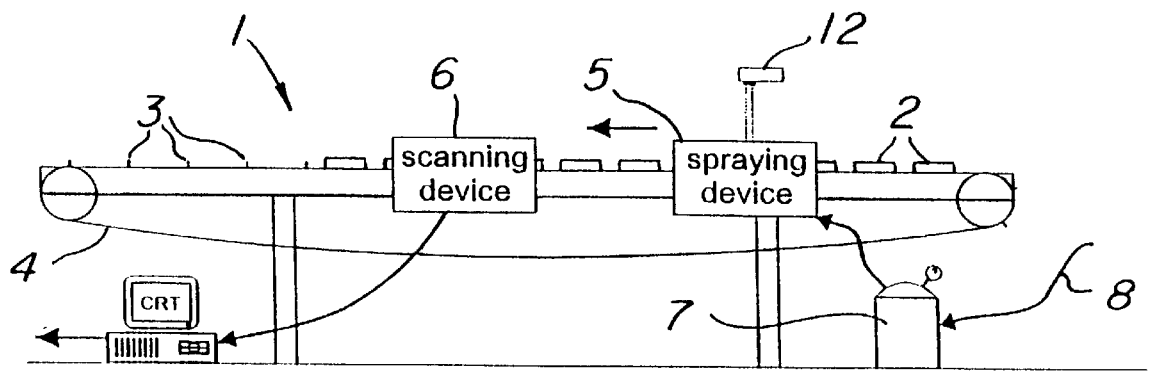
FIG. 1B is a side elevation corresponding to FIG. 1A.
Figure 2:
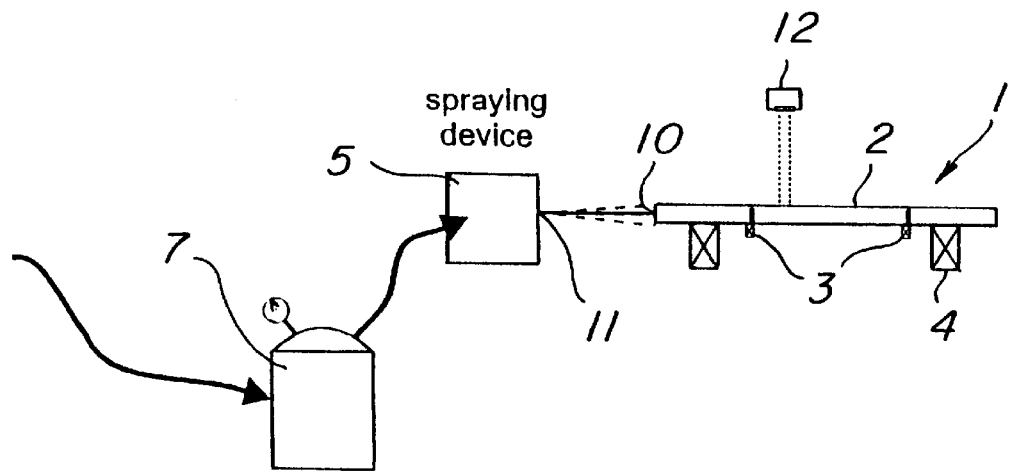
FIG. 2 is a schematic cross-sectional view illustrating the spraying station of the lumber sorting system.

The sprayer device comprises a sprayer nozzle 11 which is oriented to spray the required chemical treatment liquid on to the ends of the lumber pieces. For this purpose a scanning detector 12 positioned above the conveyor senses the approach of a lumber piece 2 as it comes into register with the spraying device and actuates the sprayer nozzle to spray the end 10 of the lumber piece, the spraying being terminated once the individual lumber piece has passed beyond the range of the detector 12.

The detector 12 has a pair of photo cells one of which responds to the leading edge of a lumber piece 2 coming into range and the other of which responds to the trailing edge of the lumber piece moving out of range. The spray flow of the nozzle 11 is arranged to cover the section of the cut end face 10 of each lumber piece with sufficient quantity to ensure that the desired chemical reaction takes place. The spraying device 5 is supplied from a tank 7 from which the required chemical is delivered, the tank being pressurized by an air compressor (not shown) coupled to the tank through a hose 8, and the spraying nozzle 11 being controlled by a valve arrangement (not shown) that responds to signals generated by the detector 12.

Since the chemical reaction takes place most reliably on freshly cut lumber, if the pieces 12 to be sorted are not freshly cut, then the apparatus can include a saw (not shown) just upstream of the spraying device 5 to produce the desired freshly cut end faces 10.

The apparatus shown in the drawings is set for differentiating lumber pieces 2 which may alternatively be of spruce or of fir. Solutions for identifying pH values are well known, as are the pH values characteristic of different wood species. For example spruce species have an average pH value of 4.5 while fir species have an average pH value of 5.4. The apparatus system described and illustrated is designed to take advantage of this difference and to apply as the chemical sprayed from the nozzle 11 bromophenol blue as an indicator. The bromophenol blue indicator reacts with the lumber pieces and turns green or blue according to whether a particular lumber piece is of spruce (average pH 4.5) or of fir (average pH 5.4). The scanning device 6 is adapted to recognize these differences in colour. The colour differences will not develop instantaneously, and accordingly the spacing of the scanning device 6 downstream of the spraying device 5 is selected in dependence upon the speed of operation of the conveyor to ensure that the desired colour characteristic has developed by the time a sprayed piece of lumber 2 reaches the scanning device.

Figure 3:
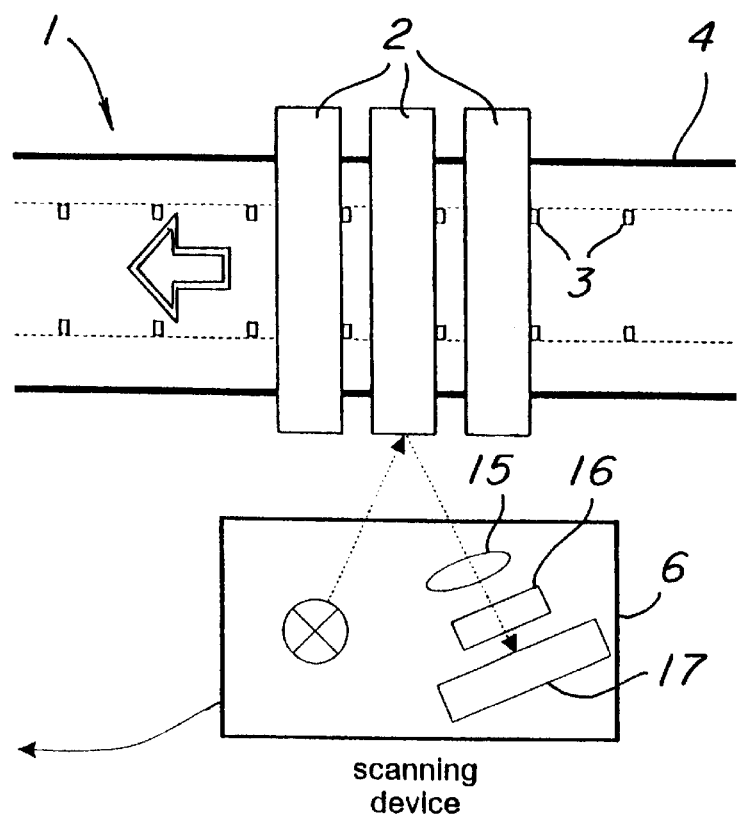
FIG. 3 is a schematic plan view illustrating the scanning device of the lumber sorting system.

The scanning device 6 is best shown in FIG. 3 and comprises a light source 13 that is aligned to direct a light beam 14 on to the ends 10 of passing lumber pieces 2. The reflected beam 14 from the end of a lumber piece is directed through a lens 15 and a filter. 16 to an optical detector 17.

An algorythm is implemented to identify and classify individual lumber pieces 2 according to species (based on predetermined sorting criteria) to develop a digital signal that is delivered to a central processing unit 18 (FIG. 4) which generates a signal that indicates the sorting class determined. This signal is utilized in determining the sorting of the species. For example a mechanical separating means could be controlled by the signal to effect removal of selected ones of the lumber pieces. Alternatively the signal could be used control a marking means for identifying specific lumber pieces that should be separated.

Figure 4:
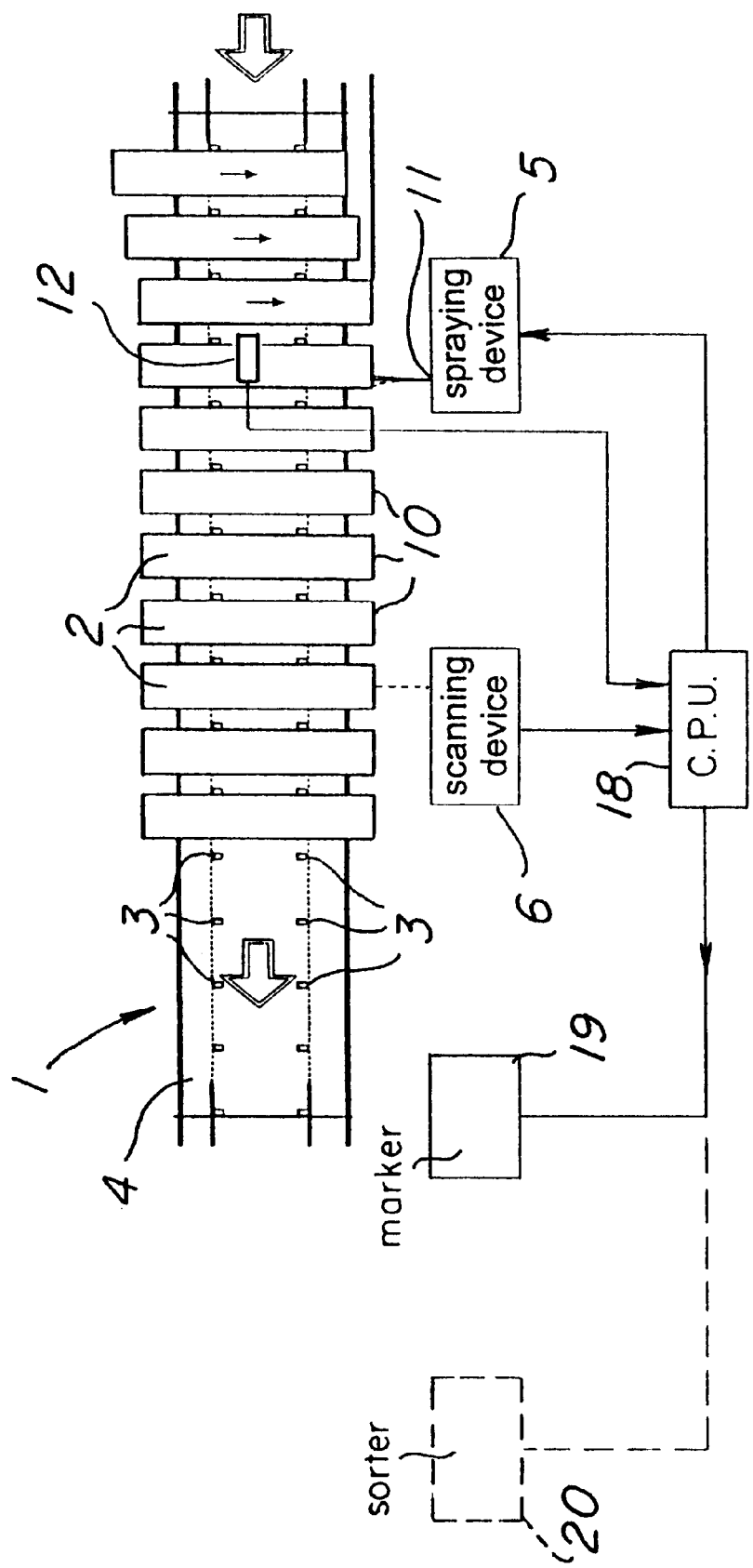
FIG. 4 is a schematic view illustrating the overall system of apparatus.

The overall system of apparatus as illustrated schematically in FIG. 4 is controlled by the central processing computer unit 18 which controls operation of the spraying device based upon signals received from the detectors 12, and which receives from the scanning device 16 the signals generated by the optical scanning of the cut ends of the lumber pieces 2, and analyses these signals in accordance with an algorythm to identify lumber pieces of a predetermined species. The CPU then delivers an output signal to a marker 19 or the like which may for example be a sprayer which applies a paint spray of predetermined colour to identify the selected lumber pieces. Alternatively, the output signal from the CPU 18 could be delivered to a mechanical sorter 20 which would operate to physically separate selected ones of the lumber pieces 2 from the remainder of the lumber pieces on the conveyor.

Although described above in relation to the separation of lumber pieces according to whether or not they are of spruce or of fir, it will be appreciated that the techniques described are applicable in many other situations where it is necessary to classify lumber pieces of different species or having different recognizable characteristics. The described technique of treating the lumber pieces to produce a characteristic colour reaction and sorting the lumber pieces based upon the resultant colours by means of detectors including a spectroscope, is clearly useful in many situations. Accordingly the invention is not limited to the specific embodiments and features discussed above, but rather is intended to encompass all systems and variations thereof included within the scope of the appended claims.

What is claimed is:

1. A method for differentiating lumber pieces to facilitate separation of pieces of one species from those of another comprising:

(a) coating a cut end of each lumber piece with an indicator liquid which is such as to react with the cut end, lumber pieces of a predetermined species producing a reaction product that is characteristic of such species;

(b) scanning the coated ends of said lumber pieces produced in step (a) and identifying pieces of said predetermined species through means for recognizing said characteristic reaction; and (c) separating such identified pieces from the remainder of said pieces.

2. The method as claimed in claim 1 wherein said characteristic reaction produces a change in the optical properties of the cut ends of pieces of said predetermined species, and said identifying is effected by a spectral analysis system.

3. The method of claim 2 wherein said indicator liquid produces a change in colour in said cut ends, and said spectral analysis system is tuned to respond to a predetermined spectral signature that is characteristic of one of said species.

4. The method of claim 1 wherein differentiating is conducted on a continuous basis, said lumber pieces being delivered on a conveyor in succession past a first station where the indicator liquid is applied and a downstream second station wherein said scanning step is effected, and a further downstream separating station wherein said Identified pieces are marked for separation.

5. The method of claim 4 wherein said liquid is applied to said cut ends by a sprayer and said scanning device applies a beam of light to the cut ends passing said scanning station, the cut ends when illuminated by said beam of light are optically scanned to produce a signal that is analyzed to identify the species of the corresponding lumber piece.

6. Apparatus for differentiating lumber pieces according to species comprising:
   (a) means for coating a cut end of each of a series of lumber pieces with an indicator liquid which reacts with said cut end to produce a reaction that is characteristic of said predetermined species;
   (b) a scanner for scanning the coated ends of said lumber pieces and for generating a signal from said characteristic reaction; and
   (c) an analyzer connected to receive said signal from said scanner and to analyze said signal to identify lumber pieces of a predetermined species.

7. The apparatus of claim 6 including a conveyor for advancing said lumber pieces in series, said means for coating comprising a sprayer positioned alongside said conveyor and operative to spray indicator liquid on to a cut end of each said lumber piece, said scanner being located adjacent said conveyor and downstream from said sprayer at a distance which is sufficient to allow time for said characteristic reaction to develop.

8. The apparatus of claim 7 further comprising means for physically identifying lumber pieces of a predetermined species.

9. The apparatus of claim 8 wherein said means for physically identifying comprises means to apply an identifying colour mark to selected ones of said lumber pieces.

10. The apparatus of claim 8 wherein said means to identify comprises a mechanical means for physically separating selected ones from the remainder of said lumber pieces.

11. The apparatus of claim 7 comprising a central processing computer unit which is connected to receive signals from said scanning device and analyze said signals in accordance with a predetermined algorithm to identify lumber pieces of a predetermined species.

12. The apparatus of claim 11 including a sensor adapted to detect the presence of a lumber piece in register with said spraying means, said central processing computer unit receiving a signal from said detector and operating said spraying means in accordance with said signal.

13. The apparatus of claim 7 including a saw that is located upstream of said sprayer to produce a fresh cross-grain cut end on each said lumber piece that is delivered past said sprayer.

14. The apparatus of claim 6 wherein said scanner comprises a light source that is adapted to project a beam of light on to a cut end of each lumber piece, together with an optical detector which is positioned to receive light that is reflected from such cut end.

15. The apparatus of claim 8 comprising: a central processing computer unit which is connected to receive signals from said scanning device and analyze said signals in accordance with a predetermined algorithm to identify lumber pieces of a predetermined species; and a sensor adapted to detect the presence of a lumber piece in register with said spraying means, said central processing computer unit receiving a signal from said detector and operating said spraying means in accordance with said signal.

16. The apparatus of claim 9 including a saw that is located upstream of said sprayer to produce a fresh cross-grain cut end on each said lumber piece that is delivered past said sprayer.

17. The apparatus of claim 7 wherein said scanner comprises a light source that is adapted to project a beam of light on to a cut end of each lumber piece, together with an optical detector which is positioned to receive light that is reflected from such cut end.

18. The apparatus of claim 8 comprising a central processing computer unit which is connected to receive signals from said scanning device and analyze said signals in accordance with a predetermined algorithm to identify lumber pieces of a predetermined species.

19. The apparatus of claim 18 including a saw that is located upstream of said sprayer to produce a fresh cross-grain cut end an each said lumber piece that is delivered past said sprayer.

20. The apparatus of claim 18 wherein said scanner comprises a light source that is adapted to project a beam of light on to a cut end of each lumber piece, together with an optical detector which is positioned to receive light that is reflected from such cut end.

* * * * *